United States Patent [19]
Sainsbury et al.

[11] Patent Number: 5,719,174
[45] Date of Patent: Feb. 17, 1998

[54] INDENOINDOLE COMPOUNDS FOR USE IN ORGAN PRESERVATION

[75] Inventors: Malcolm Sainsbury, Bristol, England; Howard G. Shertzer, Cincinnati, Ohio; Per-Ove Sjöqvist, Mölnlycke, Sweden

[73] Assignees: Astra Aktiebolag, Soldertalje, Sweden; Univ. of Bath, Bath, United Kingdom; Cincinnati, Cincinnati, Ohio

[21] Appl. No.: 318,624

[22] PCT Filed: Jul. 14, 1994

[86] PCT No.: PCT/SE94/00692

§ 371 Date: Sep. 30, 1994

§ 102(e) Date: Sep. 30, 1994

[87] PCT Pub. No.: WO95/02323

PCT Pub. Date: Jan. 26, 1995

[30] Foreign Application Priority Data

Jul. 16, 1993 [SE] Sweden .................................. 9302431

[51] Int. Cl.$^6$ ...................... C07D 209/94; C07D 209/70
[52] U.S. Cl. ............................................. 514/410; 548/420
[58] Field of Search ............................ 514/410; 548/420

[56] References Cited

U.S. PATENT DOCUMENTS

| 5,185,360 | 2/1993 | Sainsbury et al. ...................... 514/410 |
| 5,407,793 | 4/1995 | Del Nido et al. ....................... 514/561 |

FOREIGN PATENT DOCUMENTS 0409410  1/1991  European Pat. Off. .

OTHER PUBLICATIONS

Halliwell et al., Drugs vol. 42, No. 4, pp.569–605 Dec. 1991).
Halliwell et al., J. Lab. Clin. Med. vol. 119, No. 6, pp.598–620 Dec. 1992).
Swanson et al., J. Heart Transplantation vol. 7, No. 6, pp.456–467 Dec. 1988).

*Primary Examiner*—John M. Cooney, Jr.
*Attorney, Agent, or Firm*—White & Case

[57] ABSTRACT

The use of antioxidants having indenoindole structure as additives to organ preservation solutions. Such a preservation solution is useful both for in site organ treatment in the donor and for organ storage after the organ is harvested. The present invention also discloses an improved organ preservation solution.

7 Claims, No Drawings

INDENOINDOLE COMPOUNDS FOR USE IN ORGAN PRESERVATION

FIELD OF THE INVENTION

The present invention relates to the use of hydrophobic antioxidants having an indenoindole structure in medical therapy for preservation of organs in vitro as well as in vivo. Such compounds are already known to be highly efficient in reducing, i.e. quenching, free radicals in lipids or lipid biphases, thereby terminating the lipid peroxidation process and preventing conditions and diseases initiated by this or related processes. In particular the present invention is based on the use of at least one of two specific compounds or a salt thereof, preferably a therapeutically acceptable salt thereof, as an additive in a preservation solution for organs, especially a cardioplegia solution. Such a preservation solution may be used both for in situ organ treatment in the donor and for organ storage after the organ is harvested. Furthermore the invention relates to an improved preservation solution for organs.

BACKGROUND OF THE INVENTION

Some biological processes generate more or less stable intermediates that contain an unpaired electron, which can either be donated, or paired with an additional electron from the surroundings. Such intermediates are called free radicals, and they may be the products of various enzymatic and nonenzymatic reactions, some of which are vital for body functions, e.g. reduction of ribonucleoside diphosphates for DNA synthesis and the generation of prostaglandins in the prostaglandin synthetase reaction. The latter is essential for inflammatory response following cell injury, and a number of other functions. Other radical reactions include the myeloperoxidase reaction in neutrophils and macrophages which destroy bacteria and other invading particles, and the electron transport in the mitochondrial respiratory chain. Most organisms contain chemical antioxidants such as α-tocopherol (vitamin E), ascorbic acid and different radical and peroxide-inactivating enzymes, e.g. superoxide dismutase, catalase and glutathione peroxidase.

Free radicals of various types are becoming increasingly associated with a broad range of conditions and diseases such as ischemic and reperfusion injury, atherosclerosis, thrombosis and embolism, allergic/inflammatory conditions such as bronchial asthma, rheumatoid arthritis, conditions related to Alzheimer's disease, Parkinson's disease and ageing, cataract, diabetes, neoplasms and toxicity of antineoplastic or immunosuppresive agents and chemicals. One possible explanation for these conditions and diseases is that, for unknown reasons, the endogeneous protecting agents against radical damage are not sufficiently active to protect the tissue against radical damage. Lipid peroxidation caused by excess generation of radicals may constitute one significant damaging pathway in the above conditions. Inhibition of this lipid peroxidation would thus provide a way of preventing or curing the above conditions and diseases.

The general idea of using antioxidants for alleviating ischemia/reperfusion injuries have been described in several papers, for example Drugs 42(4): 569–605, 1991, and J Lab Clin Med, Vol. 119 (6): 598–620, June 1992. The possible use of indenoindoles for alleviating ischemia and reperfusion injuries as well as other conditions and diseases mention above has been proposed by M. Sainsbury and H. G. Shertzer in the patent specifications EP-A 409 410 and GB 9022453.6-A. In practice, however, it is very difficult to show any correlation between antioxidant potency and organ protecting ability. The two specific compounds which now have been found useful for preservation of organs in accordance with the present invention are prior disclosed in EP-A 409 410 and GB 9022453.6-A as well as processes for their preparation.

SUMMARY OF THE INVENTION

The present invention describes a novel use of two known specific antioxidants of the indenoindole type, which compounds fulfill both the requirement of being sufficiently hydrophobic, thus possibly accumulating in membranes, and to be potent inhibitors of lipid peroxidation. These antioxidants can be used in medical therapy for preservation of organs in vitro as well as in vivo. In comparision with other antioxidants, e.g. α-tocopherol, the two specific compounds are very favourable for the use in accordance with the present invention.

DETAILED DESCRIPTION

The two indenoindoles which now have been found to be useful as additives in organ preservation solutions are disclosed in the patent specifications mentioned above. These compounds offer a longlasting and an unexpectedly effective protection against different ischemia and reperfusion injuries. The present indenoindoles have formula I and formula II, respectively.

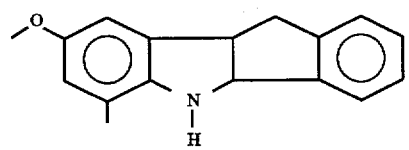

8-Methoxy-6-methyl-THII

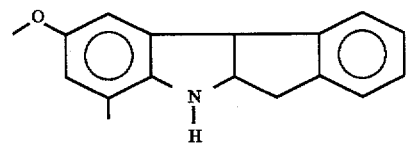

9-Mehtoxy-7-methyl-iso-THII

The compounds I and II may be used either as racemic mixtures or in the enantiomeric pure form and the invention also includes the use of the compounds in form of pharmaceutically acceptable salts thereof.

The compounds of the formula I or II may be supplemented to an organ preservation solution as such or in the form of a pharmaceutical preparation comprising the active ingredient either as a free base or a pharmaceutically acceptable non-toxic acid salt, e.g. a hydrochloride, hydrobromide, lactate, acetate, phosphate, sulfate, sulfamate, citrate, tartrate, oxalate and other salts approved by the Food and Drug Administration (FDA). The active substance is preferably supplemented to the preservation solution in a pharmaceutically acceptable dosage form.

The compounds may be converted into suitable salts using standard procedures. Thus, the free base and a suitable acid are dissolved, with or without applying heat, in an applicable solvent. Crystals are formed either spontanously, or upon cooling, are collected and washed with small portions of cold solvent. Drying and recrystallization from a suitable solvent offered the pure salts.

The dosage form may be a liquid solution ready for use or intended for dilution with a preservation solution. Alternatively, the dosage form may be lyophilized or powder filled prior to reconstition with a preservation solution. The lyophilized substance may contain, if suitable, conventional excipients.

3

The final concentration of the active substance in the preservation solution varies from about $1\times10^{-7}$ to 10% by weight of active substance.

The preservation solutions may be a preservation solutions suitable for preservation of different kind of organs such as heart, kidney and liver as well as tissues therefrom. Such a preservation solution commercially available is Plegisol and other preservation solutions named in respect of its origin are such as the UW-solution (University of Wisconsin), the Stanford solution and the Modified Collins solution, J. Heart Transplant Vol.7(6):456–467,1988. The improved preservation solution according to the invention is suitable both for in situ organ treatment in the donor and for storage of organs after harvest.

The improved preservation solutions may also contain conventional co-solvents, excipients, stabilizing agents and/or buffering agents. The preservation solutions may conveniently be provided in various dosage units.

The compounds to be used in accordance with the invention are known compounds. Compound I is described in EP-A 409 410, example 17, and compound II is described in GB 9022453.6-A, example 55. The present compounds may be prepared in accordance with the information given in the patent specifications cited above, or by other conventional processes.

Pharmacological Properties and Tests of the Compounds

The indenoindoles used for organ preservation according to the present invention are hydrophobic and stable structures which form cation radicals or radicals upon oxidation. They constitute potent antioxidants as measured by inhibition of $Fe^{2+}$ ascorbate induced lipid peroxidation in vitro, with a $IC_{50}$ value as low as 10 nM. (See EP-A 409 410). The compounds of formulas I and II prevent efficiently oxidation of lipoproteins in human plasma in the presence of rabbit smooth muscle cells or mouse peritoneal macrophages. When these compounds are used as additives to organ preservation solutions they increase organ performance and they also prevent ischemic and reperfusion damage to isolated rat heart cells, isolated perfused rat heart, rat bone marrow, rat kidney and rat liver. These properties show that the compounds of formulas I and II are useful as additives in preservation solutions for organs such as kidney, liver, heart and tissues therefrom.

The indenoindole compounds are efficient as flee-radical scavengers or antioxidants. An assay system measuring the concentration of the compounds of formulas I and II required to inhibit lipid peroxidation by 50% ($IC_{50}$) was used. The assay system, ascorbate/$Fe^{2+}$-dependent lipid peroxidation, was the same system used in EP-A 409 410 and detailed information about the system is given in said patent specification.

1. Ascorbate/$Fe^{2+}$-dependent lipid peroxidation

Table 1 shows the effects of indenoindoles and α-tocopherol on ascorbate/$Fe^{2+}$-dependent lipid peroxidation.

TABLE 1

| Compounds | $pIC_{50}$ |
| --- | --- |
| Compound I of the invention: 8-Methoxy-6-methyl-THII | 8.0 |

TABLE 1-continued

| Compounds | $pIC_{50}$ |
| --- | --- |
| Compound II of the invention: 9-Methoxy-7-methyl-iso-THII | 8.2 |
| Reference compounds: α-Tocopherol (Vitamin E) | 5.0 |
| Compound III: 4b,6,8,9b-Tetramethyl-THII (EP-A 409 410, example 15) | 7.4 |

2. In vitro hypoxia and reoxygenation of kidney tissue

Lipid peroxidation was also tested in renal tissue. Samples were obtained from anesthetized rats, cut into 2 mm slices and put into 50 ml Erlenmeyer flasks containing 40 mmol $l^{-1}$ Hepes buffer (pH 7.40) 37° C. (10–100 mg tissue per 4 ml buffer). The tissue was made hypoxic for 20 min by bubbling a fine stream of argon gas through the buffer. After that an antioxidant or the corresponding vehicle was added to the buffer and the tissue was kept under argon for an additional period of 20 min. The sample was then reoxygenated by vigourous bubbling of the buffer with 95.5% $O_2:CO_2$. After 30 min reoxygenation the iron chelator deferoxamine mesylate (Ciba Geigy AG, Basel, Switzerland) was added (final concentration 45 µmol $l^{-1}$). The sample was homogenized on ice, quickly frozen in dry-ice and alcohol and stored at –70° C. After thawing the formation of 2-thiobarbituric acid-reactive material (TBARS) was determined (Svensson et al Scand J Clin Invest 1993:53). The potencies of the antioxidants ($pIC_{50}$ i.e. –log of the concentration (antioxidant) needed to reduce TBARS formation by 50% of the corresponding vehicle value) was for compound I: 6.8 and for compound II: 6.8.

Discussion: Ex vivo protection of renal tissue subjected to hypoxia and reoxygenation In the ascorbate/$Fe^{2+}$ model compound III (an antioxidant having indenoindole structure) had a $pIC_{50}$ of 7.4 compared to 8.0 and 8.2 for compounds I and II, respectively. When compounds I and II were administered to mice in an oral dose of 50 mg/kg, they abolished lipid peroxidation in renal tissue, subjected to ex vivo hypoxia and reoxygenation, up till 6 h after administration. In contrast, other compounds with the indenoindole structure like compound III showed only weak inhibitory effect on lipid peroxidation, which could be detected only up to 30 min after administration. These results show that compounds I and II have unique properties being effective for in vivo treatment of lipid peroxidation.

3. Inhibition of reoxygenation damage in isolated heart cells and isolated hearts

3.1 Isolated heart cells

Hearts were collected from 2 and 6 days old rats and the ventricles were dissected free, placed in Hanks balanced salt solution without $Ca^{2+}$ and $Mg^{2+}$ but with 0.35 g/l sodium-carbonate and cut in small pieces. The cells were dispersed in the same solution but supplemented with collagenase solution (type 1, 0.8 mg/ml) at 37° C. for 10 minutes and centrifuged, 160 xg for 5 minutes. Subsequently, 5 serial 20 minutes digestions were performed. The cells from the initial digestion were discarded. Centrifugation was made after each 20 minutes period and the collage nase solution was changed to Ham's F 10 culture medium, supplemented with 10% fetal bovine serum (FBS), glutamine 2 mM, penicillin 50 IU/ml and streptomycin 50 µg/ml. A modified method to enrich the isolation of myocytes, were used, including replaiting the cells twice for 30 and 90 min, respectively. The myocytes were plated on 35 mm plastic culture dishes at a density of approximately $9\times10^5$ cells/ml ($1.8\times10^6$ cells/dish). The cells were kept in culture for 6 days at 37° C. and 5% $CO_2$ under aerobic conditions in a Forma Scientific carbon dioxide incubator, 5% $CO_2$. During this period the cells reached confluence and were beating spontaneously at an approximate frequency of 20–40 beats/min. Each culture dish contained 0.9±0.2 mg protein. The supplemented F10-medium was changed each day. The antioxidant compound II was added to the culture medium in ethanol, reaching a final concentration of 0.1% ethanol. The final concentration of compound II in the culture medium was 0.01, 0.1, 1.0 or 5.0 µmol/l. Before starting the experiment the medium above the myocytes were removed and changed to fresh F10-medium supplemented with glutamine, which was made hypoxic by argon bubbling for 1 hour before addition to the cells. The culture plates were transferred to specially designed air tight thermostated chambers. The experiment lasted for 300 min including 60 min hypoxia, when nitrogen (95% $N_2$, 5% $CO_2$) was slowly gassed above the cells, followed by 240 min reoxygenation (95% $O_2$, 5% $CO_2$). Cell viability was determined by leakage of LD into the medium, and was analyzed after various times 1, 30, 60, 90, 120, 180, 240 and 300 min. The results showed that at a concentration of 1 µmol/l (compound II) reduced the damage (LD-leakage) by 90% and the calculated $pIC_{50}$ ($-logIC_{50}$) value was 7.5.

3.2 Improved postischemic recovery of the heart

Experiments were designed to investigate the effect on the myocardial recovery after six hours cold ischemia when an antioxidative agent compound II, was added to a crystalloid cardioplegic solution, such as Plegisol (Abbott). The retrogradely perfused (Langendorff) isolated rat heart with an intra-ventricular balloon was used. The hearts were single flushed perfused (10 ml, 4° C.) with either plain Plegisol or Plegisol supplemented with 1 µmol/l of compound II. The hearts were then stored for 6 hours in the respective solution at 4° C. In a third group hearts were single flush perfused with Plegisol without storage of the hems. In the group of hearts treated with compound II supplemented Plegisol the postischemic left ventricular developed pressure (LVDP= calculated as the difference between peak systolic and end-diastolic pressure) was significantly improved with a LVDP of 90±9% (% of preischemic value, mean±SEM) compared to 57±11% in hearts preserved with plain Plegisol. Single flush perfusion without storage resulted in LVDP of 89±1%.

This study shows that addition of compound II to a heart preservation solution, such as Plegisol, drastically improves the functional recovery of rat hearts and could be beneficial in clinical heart transplantation as well as other organ transplantations.

We claim:

1. A method for organ preservation which comprises treating an organ with an organ preservation solution to which has been added an indenoindole compound selected from the group consisting of 8-methoxy-6-methyl-THII and 9-methoxy-7-methyl-iso-THII, or a pharmaceutically acceptable salt thereof, in the form of a racemic mixture or an enantiomer.

2. The method according to claim 1 for in situ treatment of organs in an organ donor.

3. A method of using an indenoindole compound selected from the group consisting of 8-methoxy-6-methyl-THII and 9-methoxy-7-methyl-iso-THII, or a pharmaceutically acceptable salt thereof, in the form of a racemic mixture or an enantiomer, for preparing an organ preservation solution for in situ treatment of organs in an organ donor which comprises adding the indenoindole compound to an organ preservation solution.

4. The method according to claim 1 for storage of organs in vitro.

5. The method according to claim 1 wherein the indenoindole compound is 8-methoxy-6-methyl-THII.

6. The method according to claim 1 wherein the indenoindole compound is 9-methoxy-7-methyl-iso-THII.

7. The method according to claim 1 wherein the organ preservation solution is a cardioplegia solution.

* * * * *